(12) United States Patent
Spielmann et al.

(10) Patent No.: US 10,577,312 B2
(45) Date of Patent: *Mar. 3, 2020

(54) PROCESS FOR PURIFYING ALKANESULFONIC ACIDS

(71) Applicant: BASF SE, Ludwigshafen am Rhein (DE)

(72) Inventors: Jan Spielmann, Mannheim (DE); Michael Koch, Speyer (DE); Juergen Wortmann, Limburgerhof (DE); Feely Ruether, Frankenthal (DE); Sabine Weiguny, Freinsheim (DE); Frieder Borgmeier, Mannheim (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/774,847

(22) PCT Filed: Nov. 8, 2016

(86) PCT No.: PCT/EP2016/076958
§ 371 (c)(1),
(2) Date: May 9, 2018

(87) PCT Pub. No.: WO2017/080991
PCT Pub. Date: May 18, 2017

(65) Prior Publication Data
US 2018/0319739 A1    Nov. 8, 2018

(30) Foreign Application Priority Data
Nov. 10, 2015   (EP) ..................... 15193899

(51) Int. Cl.
*C07C 303/44*    (2006.01)
*C07C 309/01*    (2006.01)
(Continued)

(52) U.S. Cl.
CPC ............ *C07C 303/44* (2013.01); *B01D 3/007* (2013.01); *B01D 3/143* (2013.01); *B01D 9/0045* (2013.01);
(Continued)

(58) Field of Classification Search
CPC ...... B01D 3/14; B01D 9/0004; B01D 9/0009; B01D 9/0013; C07C 309/01;
(Continued)

(56) References Cited

U.S. PATENT DOCUMENTS 2,518,639 A * 8/1950 Proell .................. C07C 303/44
                                                      562/124
4,035,242 A    7/1977 Brandt
(Continued)

FOREIGN PATENT DOCUMENTS

CN    1810780 A    8/2006
DE    26 43 000 A1    3/1977
(Continued)

OTHER PUBLICATIONS

Sigma-Aldrich, "Methanesulfonic Acid ≥ 99.5%", Mar. 5, 2013 (date obtained from WayBack Machine), avialble online at: http://www.sigmaaldrich.com/catalog/product/sial/471356?lang=en®ion= (Year: 2013).*

(Continued)

*Primary Examiner* — Jonathan Luke Pilcher
(74) *Attorney, Agent, or Firm* — Oblon, McClelland, Maier & Neustadt, L.L.P.

(57) ABSTRACT

A process comprising: (a) distilling a melt comprising crude alkanesulfonic acid to completely or partly remove low boilers, wherein the low boilers are drawn off at the top of a distillation column or of a one-stage evaporation apparatus and a material stream comprising alkanesulfonic acid, high boilers and residual low boilers is withdrawn at the bottom (Continued)

of the distillation column or of the one-stage evaporation apparatus, (b) sending the stream comprising alkanesulfonic acid, high boilers and residual low boilers into a melt crystallization as the starting melt to obtain crystals formed from the alkanesulfonic acid, hydrates of the alkanesulfonic acid or a mixture of both suspended in mother liquor, (c) performing a solid-liquid separation to remove the crystals from the mother liquor, and (d) optionally washing the crystals to remove mother liquor adhering to the crystals.

20 Claims, 2 Drawing Sheets

(51) Int. Cl.
    *C07C 309/02*     (2006.01)
    *C07C 309/03*     (2006.01)
    *B01D 3/14*     (2006.01)
    *B01D 9/00*     (2006.01)
    *B01D 3/00*     (2006.01)

(52) U.S. Cl.
    CPC .............. *B01D 3/14* (2013.01); *B01D 9/0004* (2013.01); *B01D 2009/0086* (2013.01); *C07C 309/01* (2013.01); *C07C 309/02* (2013.01); *C07C 309/03* (2013.01)

(58) Field of Classification Search
    CPC ... C07C 309/02; C07C 309/03; C07C 309/04; C07C 309/05; C07C 309/25; C07C 303/42; C07C 303/44; C07C 303/46
    USPC ........................................................ 562/124
    See application file for complete search history.

(56) References Cited

U.S. PATENT DOCUMENTS

| | | | |
|---|---|---|---|
| 4,450,047 A | 5/1984 | Malzahn | |
| 4,686,097 A * | 8/1987 | Horoldt | C07C 303/42 208/13 |
| 4,938,846 A | 7/1990 | Comstock et al. | |
| 5,107,019 A * | 4/1992 | Gallistru | C07C 303/44 562/124 |
| 5,583,253 A * | 12/1996 | Henderson | C07C 303/44 562/115 |
| 6,060,621 A | 5/2000 | Biertuempel et al. | |
| 6,337,421 B1 | 1/2002 | Gancet | |
| 7,112,695 B2 * | 9/2006 | Eck | B01D 9/0013 562/598 |
| 9,440,915 B2 * | 9/2016 | Yi | C07C 303/02 |
| 10,214,485 B2 * | 2/2019 | Spielmann | C07C 303/44 |
| 2010/0087674 A1 * | 4/2010 | Reinhardt | C07C 303/14 562/124 |

FOREIGN PATENT DOCUMENTS

| | | |
|---|---|---|
| DE | 890 02 877 T2 | 1/1994 |
| DE | 197 43 901 C1 | 4/1999 |
| DE | 10 2007 020 697 A1 | 11/2008 |
| EP | 0 373 305 A1 | 6/1990 |
| EP | 0 405 289 A1 | 1/1991 |
| EP | 0 505 692 A1 | 9/1992 |
| EP | 0 675 107 A1 | 10/1995 |
| GB | 1 350 328 | 4/1974 |
| WO | WO 00/31027 A1 | 6/2000 |
| WO | WO 2004/101860 A1 | 11/2004 |
| WO | WO 2005/069751 A2 | 8/2005 |
| WO | WO 2015/071365 A1 | 5/2015 |
| WO | WO 2015/086645 A1 | 6/2015 |

OTHER PUBLICATIONS

Wang, Liming, "Clusters of Hydrated Methane Sulfonic Acid CH3SO3H,(H2O)n (n ) 1-5): A Theoretical Study", J. Phys. Chem. A 2007, 111, 3642-3651, available online at: https://pubs.acs.org/doi/10.1021/jp067893n (Year: 2007).*

U.S. Appl. No. 15/033,296, filed Sep. 15, 2016, 2016/0264509, Kaller et al.

U.S. Appl. No. 15/321,257, filed Jul. 20, 2017, 2017/0205151, Wortmann et al.

U.S. Appl. No. 15/774,722, filed May 9, 2018, Spielmann et al.

International Search Report dated Jan. 27, 2017 in PCT/EP2016/076958, 3 pages.

Berthoud, A., "Quelques Proprietes Physico-Chemique Des Acides Ethane—Et Methane—Sulfonique", Helv. Chim. Acta. XP002765992. vol. 12, 1929, pp. 859-885.

Craig, R.A., et al., "Cryoscopic Studies in Methanesulfonic Acid", Journal of the American Chemical Society, vol. 72, Jan. 1950, pp. 163-166.

* cited by examiner

PROCESS FOR PURIFYING ALKANESULFONIC ACIDS

CROSS-REFERENCE TO RELATED APPLICATIONS

This application is a National Stage Entry of PCT/EP2016/076958, which was filed Nov. 8, 2016, and claims priority to EP 15193899.0, which was filed Nov. 11, 2015.

BACKGROUND OF THE INVENTION

The invention proceeds from a process for purifying alkanesulfonic acids.

Alkanesulfonic acids, in particular methanesulfonic acid (MSA), are employed in myriad applications in pure form and in admixture with water and other solvents. The use of MSA is particularly widespread in electroplating, tinplate production and wire tinning. Alkanesulfonic acids are also employed as solvent or as catalyst in alkylation and esterification reactions for example. A further field of application for alkanesulfonic acids is the production of biodiesel where the typically employed sulfuric acid may be replaced by alkanesulfonic acids on account of the improved performance properties of the latter.

Alkanesulfonic acids are also an alternative to phosphoric-acid-containing cleaning product formulations. Since methanesulfonic acid in particular forms readily soluble salts and is readily biodegradable, the alternative use of alkanesulfonic acid can play a role in water pollution control.

Hereinbelow, all components of crude alkanesulfonic acid other than alkanesulfonic acid and water are encompassed by the term "impurities". The term "low boilers" is to be understood as meaning water and all components having a boiling point below the boiling point of alkanesulfonic acid. The term "high boilers" is to be understood as meaning all components having a boiling point above the boiling point of alkanesulfonic acid. The alkanesulfonic acid is in particular methanesulfonic acid.

The production of alkanesulfonic acids initially generates crude alkanesulfonic acid. This is a mixture of alkanesulfonic acid, low boilers and high boilers, the low boilers and high boilers varying depending on the production process. Low boilers are generally water, nitric acid, hydrochloric acid, thioesters, alkanesulfonyl chloride, sulfur trioxide, alkanes and alkylsulfones. High boilers often include sulfuric acid, alkanedisulfonic acids or chloroalkanesulfonic acid. Color-conferring substances may also be present.

To obtain pure alkanesulfonic acid or aqueous solutions of alkanesulfonic acid the crude alkanesulfonic acid is typically purified by distillation, nanofiltration, selective absorption of impurities over exchange resins or selective precipitation of impurities as salts. Of these, distillation is the dominant process, stripping being regarded as a distillative or evaporative process and distillation typically being performed at pressures below atmospheric pressure, since alkanesulfonic acid may form decomposition products at the temperatures required for distillation at atmospheric pressure. For example, distillative purification of methanesulfonic acid may lead to the formation of methyl methanesulfonate. A further problem is that methanesulfonic acid is corrosive at the high temperatures necessary and only a limited choice of stable materials of construction is available.

WO-A 00/31027 discloses the production of alkanesulfonic acid by oxidation of alkyl mercaptans, dialkyl disulfides or dialkyl polysulfides with nitric acid. This generates nitrogen oxides, water and further byproducts such as sulfuric acid. The nitric acid is regenerated from the nitrogen oxides by oxidation with oxygen and recycled into the process. To purify the product, low boilers and high boilers are removed by distillation in two stages to obtain pure, practically anhydrous alkanesulfonic acid. Water and nitric acid are removed from the crude product in a water removal column operated as a stripping column at slightly reduced pressure. The bottoms product obtained comprises 1 wt % water and about 1 wt % high boilers, especially sulfuric acid. The removal of the high boilers is achieved by distillation of the alkanesulfonic acids with purities of greater than 99.5 wt % and sulfuric acid contents of less than 50 ppm under high vacuum, i.e. at a pressure of from 0.1 to 20 mbar (abs).

WO-A 2015/086645 describes the production of alkanesulfonic acid by oxidation of dialkyl disulfides with nitrogen oxides. The nitrogen oxides are regenerated with oxygen-enriched air for example. The reaction products are subsequently freed of low and high boilers via two distillation columns. The thus purified product comprises an unspecified concentration of methanesulfonic acid.

GB-A 1350328 describes the synthesis of alkanesulfonic acids by chlorination of alkyl mercaptans or dialkyl disulfides in aqueous HCl. The product of the reaction is alkanesulfonic acid in 70 to 85 wt % purity. This document describes a two-stage process for producing anhydrous methanesulfonic acid. This comprises a first step in which water is distilled off and a second step in which the methanesulfonic acid is distilled out of the bottoms product with a short column and obtained overhead.

WO-A 2005/069751 describes the synthesis of methanesulfonic acid from sulfur trioxide and methane via a free-radical chain reaction with for example Marshall's acid as free-radical initiator. In this synthesis, anhydrous methanesulfonic acid is formed, but no information is given about purification. WO-A 2015/071365 describes a similar process, with distillation being suggested for purifying the resulting methanesulfonic acid. The product of this production process is mostly free from water. However, it comprises sulfur trioxide.

CN-A 1810780 describes the synthesis of methanesulfonic acid by reaction of ammonium sulfite with dimethyl sulfate. This affords ammonium methylsulfonate and ammonium sulfate. Addition of calcium hydroxide forms soluble calcium methylsulfonate and insoluble calcium sulfate which may be removed easily. Sulfuric acid is added to liberate methanesulfonic acid and once again form and precipitate calcium sulfate. The aqueous solution formed is initially subjected to distillation to remove water and then subjected to distillation under reduced pressure to obtain methanesulfonic acid.

DE-C 197 43 901 describes the synthesis of methanesulfonic acid by reaction of sulfite ions with dimethyl sulfate. These sulfite ions are reacted in an aqueous system at elevated temperature and exposed to a strong acid. Sulfate is formed as a byproduct, for example in the form of sodium sulfate. Purification of the acid is by distillation.

EP-A 0 675 107 describes a process for continuous production of alkanesulfonyl chloride (ASC) or alkanesulfonic acid (ASA) by reacting an alkane mercaptan or a dialkane disulfide with chlorine in aqueous hydrochloric acid at elevated pressure. Hydrogen chloride (HCl) and other low boilers not condensable under the process conditions are desorbed after decompression of the superatmospheric pressure. ASC is produced at a preferred temperature range of from 10° C. to 35° C. and purified by means of a distillation column. ASA is obtained from ASC by hydrolysis at temperatures of from greater than 80° C. to 135° C. in the presence of water. The purification of ASC and/or ASA is also carried out with a vapor stripper for example, residual ASC also being hydrolyzed therein.

The removal of water from aqueous methanesulfonic acid by evaporation of the water in a falling film evaporator at reduced pressure is described in U.S. Pat. No. 4,450,047. Water is drawn off overhead and a product stream comprising more than 99.5 wt % methanesulfonic acid is obtained.

U.S. Pat. No. 4,938,846 discloses the removal of water from aqueous methanesulfonic acid by evaporation of the water in two falling-film evaporators arranged in series and both operated at reduced pressure.

The disadvantage of the prior art distillation processes is that the process is highly energy intensive on account of the high temperatures and the required reduced pressure. In addition, it is not possible to remove high boilers such as sulfuric acid without particularly energy intensive conversion of the alkanesulfonic acid into the gas phase. Also, certain purification processes achieve the distillation task with falling film evaporators which are useable on a large industrial scale only with difficulty.

U.S. Pat. No. 4,035,242 discloses a likewise very energy intensive process where aqueous methanesulfonic acid is purified in a two-stage distillation process. In the first distillation column a large part of the water is removed as a low boiler at reduced pressure. The bottoms product comprising methanesulfonic acid is evaporated and separated in a second rectification column at reduced pressure to obtain the methanesulfonic acid.

U.S. Pat. No. 6,337,421 discloses the removal of sulfuric acid from methanesulfonic acid using basic anion exchange resins. Other processes of removing sulfuric acid are also described, for example distillation or fractionating crystallization and also separation by nanofiltration, but none of these achieve adequate results according to the description of U.S. Pat. No. 6,337,421.

The purification of methanesulfonic acid comprising oxidizable compounds is described in EP-A 0 505 692 and EP-A 0 373 305. EP-A 0 505 692 discloses supplying chlorine to convert the impurities into methanesulfonyl chloride which is hydrolyzed to afford methanesulfonic acid and HCl in a further step. EP-A 0 373 305 discloses supplying ozone which converts methyl thiosulfate into methanesulfonic acid. However, the disadvantage of these two processes is that high-boiling components such as sulfuric acid cannot be removed, thus necessitating further purification steps.

The fractionating crystallization of methanesulfonic acid and also of ethanesulfonic acid is known in principle from R. A. Craig et al., J. Am. Chem. Soc., 1950, Vol. 72, pages 163 bis 164 or A. Berthoud, Helv. Chim. Acta, 1929, Vol. 12, page 859, but no indication is given as to how the processes described therein could be implemented in production and purification processes on a large industrial scale.

BRIEF SUMMARY OF THE INVENTION

The present invention accordingly has for its object the provision of a process which is less energy intensive than the prior art processes, which allows sufficient purification of alkanesulfonic acids and enables removal of all impurities, and which may be implemented on a large industrial scale.

DETAILED DESCRIPTION OF THE INVENTION

This object is achieved by a process for purifying alkanesulfonic acids which comprises the steps of:

(a) distilling a melt comprising crude alkanesulfonic acid to completely or partly remove low boilers, wherein the low boilers are drawn off at the top of a distillation column or of a one-stage evaporation apparatus and a material stream comprising alkanesulfonic acid, high boilers and residual low boilers is withdrawn at the bottom of the distillation column or of the one-stage evaporation apparatus, (b) sending the stream comprising alkanesulfonic acid, high boilers and residual low boilers into a melt crystallization as the starting melt to form crystals of the alkanesulfonic acid, of hydrates of the alkanesulfonic acid or of a mixture of both suspended in mother liquor, (c) performing a solid-liquid separation to remove the crystals from the mother liquor, (d) optionally washing the crystals to remove mother liquor adhering to the crystals.

It has now been found that, surprisingly, the combination of a distillation to completely or partly remove low boilers and a subsequent melt crystallization makes it possible to remove impurities from the alkanesulfonic acid while simultaneously reducing the necessary energy requirements compared to prior art processes for purifying alkanesulfonic acid. The process according to the invention further permits production both of various alkanesulfonic acids and of hydrates of alkanesulfonic acids.

Another advantage is that, in contrast to hitherto employed processes of distillative purification of alkanesulfonic acid, the process according to the invention makes it possible to achieve high purities in simple fashion in particular in the purification of methanesulfonic acid. Thus, for example, the proportion of methyl methanesulfonate in the product may be markedly reduced in the process according to the invention. The process according to the invention moreover also removes the majority of high boilers from the alkanesulfonic acid which is achieved in the prior art only through energy intensive distillation by converting the alkanesulfonic acid into the gas phase.

In accordance with the invention the distillation in step (a) also comprises a simple gas removal from liquids which may also comprise solids. Such a gas removal is for example a flash process which takes place for example during a decompression of a pressurized liquid when low boilers are transferred into the gas space after a pressure reduction.

The distillation may be performed either in a distillation column or in a one-stage evaporation apparatus. When the term "distillation column" is used hereinbelow it is also always alternatively possible to employ a one-stage evaporation apparatus, for example a falling film evaporator, a thin film evaporator, a rotary evaporator or any other evaporator known to one skilled in the art.

The crude alkanesulfonic acid supplied in step (a) originates from a conventional process for producing alkanesulfonic acids. Appropriate processes are described in WO-A 00/31027, GB-A 1350328, EP-A 0 675 107, CN-A 1810780 or WO-A 2015/071365 for example. Depending on the production process employed the crude alkanesulfonic acid comprises different low boilers and high boilers as impurities.

Low boilers typically present in crude alkanesulfonic acid, in particular crude methanesulfonic acid, include, for example, water, short-chain hydrocarbons having 1 to 8 carbon atoms, short-chain alcohols having 1 to 8 carbon atoms, nitric acid, hydrochloric acid, chlorine, alkyl mercaptans, dialkyl disulfides, dialkyl polysulfides, esters, for example methyl methanesulfonate, partly and fully chlorinated alkanesulfonic acids, methanesulfonyl chloride, sulfur dioxide, ammonia, dimethyl sulfate, monomethyl sulfate and dimethyl sulfone. The process described in WO-A 00/31027 typically generates water, alkyl mercaptans, dialkyl disulfides, dialkyl polysulfides, alkyl alkanethiosulfonates such as methyl methanethiosulfonate, alkyl alkanethiosulfinates, dialkyl disulfoxide, $C_1$-$C_x$-alcohols, nitric acid, nitrogen oxides, methyl methanesulfonate and sulfur dioxide as low boilers. Typical low boilers in the process described in GB-A 1350328 are water, alkyl mercaptans, dialkyl disulfides, dialkyl polysulfides, alkyl alkanethiosulfonates such as methyl methanethiosulfonate, alkyl alkanethiosulfinates, dialkyl disulfoxides, alkanesulfonyl halides such methanesulfonyl chloride, halogens such as chlorine or bromine, hydrogen halides such as hydrogen chloride or hydrogen bromide, C-halogenated methanesulfonic acid compounds, methyl methanesulfonate and sulfur dioxide. High boilers typically present in the process described in CN-A 1810780 are water, ammonia, methanol, dimethyl sulfate, monomethyl sulfate, sulfur dioxide and methyl methanesulfonate. In the production processes that are not water-free, water generally forms the largest proportion of the low boilers in each case.

In water-free production processes for alkanesulfonic acids, examples of conventional high boilers are short-chain hydrocarbons having 1 to 8 carbon atoms, sulfur trioxide, sulfur dioxide, impurities from feedstocks, e.g. from the methane used, initiators and the decomposition products thereof and by-products of the reaction, for example carbon monoxide or carbon dioxide.

High boilers present in the crude alkanesulfonic acid, in particular methanesulfonic acid, generally include sulfuric acid, alkanedisulfonic acid, in particular methanedisulfonic acid, long-chain hydrocarbons, inorganic salts such as sodium sulfate, sodium hydrogensulfate, sodium methylsulfate, ammonium sulfite, ammonium methylsulfate, calcium hydroxide, calcium sulfate, calcium methylsulfate. Similarly to the low boilers, the high boilers present in the crude alkanesulfonic acid also depend on the production process. Thus, for example, sulfuric acid in particular is present as a high boiler in the processes described in WO-A 00/31027, in DE-C 197 43 901 and in GB-A 1350328.

In a number of production processes, for example the process described in WO 2004/101860, dialkyl polysulfides may also be present, these occurring as high boilers or low boilers depending on their sulfur content. By contrast, the crude alkanesulfonic acid produced by the process according to CN-A 1810780 comprises ammonium sulfite, ammonium sulfate, ammonium salts of alkanesulfonic acid, calcium salts of alkanesulfonic acid, sulfuric acid, calcium sulfate and ammonium hydrogensulfate as high boilers.

The crystallization allows the impurities present in the crude alkanesulfonic acid to be removed. Said impurities accumulate in the mother liquor during the crystallization. Whether alkanesulfonic acid or the hydrate of alkanesulfonic acid crystallizes is dependent in particular on the water content in the starting melt.

Chemical processes which produce alkanesulfonic acid in water-free fashion, for example in accordance with WO-A 2015/071365, do not comprise water as a low boiler. Accordingly, it is possible to obtain the pure methanesulfonic acid by crystallization and, after addition of water, to obtain methanesulfonic acid hydrate by crystallization.

The complete or partial removal of the low boilers via the distillation in step (a) has the further advantage that this elevates the melting point of the starting melt of crude alkanesulfonic acid for the subsequent melt crystallization. The starting melt consequently requires less intense cooling, thus allowing cooling energy savings to be made.

Since a crystallization and subsequent solid-liquid separation cannot generally achieve complete removal of the product from the starting melt, the mother liquor exiting the crystallizer still comprises a large proportion of product. It is therefore preferable when the alkanesulfonic-acid-depleted mother liquor exiting the crystallizer is completely or at least partly recycled back into the process for purifying alkanesulfonic acids. Here, the alkanesulfonic-acid-depleted mother liquor may either be passed back into the crystallizer, referred to as the crystallization cycle, or else be completely or partly passed back into the distillation, referred to as the distillation cycle. Recycling into the distillation has the advantage that low boilers which accumulate in the mother liquor due to removal of the product are likewise removed.

It is preferable when the entirety of the mother liquor which is removed from the crystallizate in step (c) or runs off from the crystallizer is recycled into the distillation in step (a) or into the melt crystallization.

When the washing of the crystals in step (d) is additionally carried out, impurified washing liquid is generated which is recycled into the process for purifying alkanesulfonic acids. In this case it is preferable when the washing liquid is combined with the mother liquor.

Since crystallization of the alkanesulfonic acid causes high boilers to accumulate in the mother liquor particularly in the case of recycling into the distillation or into the melt crystallization, it is moreover preferable when the mother liquor removed in step (c) is at least partly sent to a high boilers removal to remove high boilers from the mother liquor. After removal of the high boilers the mother liquor is recycled into the process for purifying alkanesulfonic acids. The sending of the mother liquor into the high boilers removal and subsequent recycling into the process for purifying alkanesulfonic acids is referred to as the high boilers cycle. This high boilers removal is preferably effected before introduction of the mother liquor into the distillation in step (a) or into the melt crystallization. It is particularly preferable when the mother liquor after removal of the high boilers is recycled into the distillation in step (a). This makes it possible for low boilers remaining in the mother liquor as impurities to likewise be removed from the mother liquor in the distillation. In an alternative option the mother liquor after removal of the high boilers is partly condensed and the condensed portion is recycled into the distillation in step (a) and the uncondensed portion is discharged from the process as low boilers. In the case of recycling of the condensed portion of the mother liquor into the distillation in step (a) the partial condensation of the mother liquor and the discharging of the uncondensed portion of low boilers reduces the proportion of low boilers to be removed in the distillation thus allowing the distillation as a whole to be configured for a reduced throughput which in turn makes it possible to make capital expenditure savings and, in particular, energy savings.

Alternatively, it is possible to limit the concentration of low boilers in the mother liquor by discharging parts of the mother liquor and, for example, processing them as a waste stream and/or utilizing them in some way.

High boilers removal may be realized, for example, via an evaporation. This evaporates the low boilers present in the mother liquor, the alkanesulfonic acid and the high boilers remaining in the liquid phase. In order not to impair the alkanesulfonic acid and to allow the evaporation to be carried out at the lowest possible temperatures the evaporation is preferably carried out at a pressure below atmospheric pressure. The alkanesulfonic-acid-comprising vapors formed during the evaporation are preferably condensed and passed back into the distillation in step (a) or into the melt crystallization in step (b) as a liquid. Condensation of the vapors also provides the option of removing low boilers. In this case the condensation is carried out such that the alkanesulfonic-acid condenses while the low boilers remain in the gas phase. The alkanesulfonic-acid-comprising liquid phase and the low-boiler-comprising gas phase may then be separated in a gas-liquid phase separator and the low boilers present in the gas phase may be discharged from the process. An evaporation may also be facilitated by an entraining gas in the context of a stripping.

The high-boiler-comprising fraction generated in the evaporation generally also comprises a proportion of alkanesulfonic acid which may optionally be recovered in a subsequent purification step.

Both the distillation in step (a) and the evaporation of the alkanesulfonic acid to remove high boilers are carried out at a pressure below atmospheric pressure. It is preferable when the distillation in step (a) and the evaporation to remove high boilers is carried out at a pressure in the range from 5 to 500 mbar (abs), preferably from 10 to 100 mbar (abs). This allows for distillation/evaporation that is gentle toward the alkanesulfonic acid product. At higher pressures the necessary temperatures for the distillation/evaporation would be of a magnitude such that product impairment, in particular decomposition of the alkanesulfonic acid, cannot be ruled out. It is known that distillation processes using entraining agents, so-called stripping processes, may be carried out at higher pressures. This procedure is regarded as equivalent to the use of subatmospheric pressure in the context of the invention.

When the alkanesulfonic acid is methanesulfonic acid produced in a water-free process, the starting melt comprises no water but sulfur trioxide. To crystallize pure methanesulfonic acid the low boilers removal is to be carried out such that the starting melt has a concentration of methanesulfonic acid from more than 87 mol % preferably more than 92 mol % and particularly preferably 93 to 98 mol %.

When the alkanesulfonic acid is methanesulfonic acid which is produced by a process not being water-free and pure methanesulfonic acid is to be crystallized from the methanesulfonic acid and water comprising starting melt, low boilers removal is to be carried out such that the starting melt has a concentration of methanesulfonic acid of at least 76 mol %, preferably at least 82 mol % and particularly preferably at least 90 mol %. The pressure and temperature settings for the low boilers removal may thus be varied within wide limits but are related to one another via substance-specific vapor pressure curves. The particularly preferred value for the methanesulfonic acid concentration in a methanesulfonic acid/water mixture of 90 mol % is achievable in a preferred pressure range of from 40 to 130 mbar (abs) and the corresponding bottoms temperature ranges of from 160° C. to 200° C. The reported temperature range is typically around 10 to 20 K higher than specified by physical substance-specific properties since flow in the column may give rise to pressure drops and insulation weaknesses may give rise to heat losses.

When the alkanesulfonic acid is methanesulfonic acid and methanesulfonic acid hydrate is to be crystallized, low boilers removal is to be carried out such that the starting melt comprising methanesulfonic acid and water has a concentration of methanesulfonic acid of 31 to 75 mol %, preferably 45 to 63 mol % and particularly preferably 47 to 55 mol %. Here too, the pressure and temperature settings for the low boilers removal may be varied within wide limits. A particularly preferred value for the methanesulfonic acid concentration of 51 mol % is achievable, for example, at a pressure of from 40 to 130 mbar (abs) and a bottoms temperature of from 80° C. to 120° C.

When the alkanesulfonic acid is ethanesulfonic acid which is produced in a process not being water-free and pure ethanesulfonic acid is to be crystallized, low boilers removal is to be carried out such that the starting melt comprising ethanesulfonic acid and water has a concentration of ethanesulfonic acid of at least 76 mol %, preferably at least 82 mol % and particularly preferably at least 90 mol %. The pressure and temperature settings for the low boilers removal may thus be varied within wide limits as in the production of methanesulfonic acid. Since ethanesulfonic acid has a markedly lower vapor pressure than methanesulfonic acid, the preferred distillation pressures are correspondingly lower. An alternative increase of the distillation temperatures greatly in excess of 200° C. is problematic on account of appreciable ethanesulfonic acid decomposition.

When the alkanesulfonic acid is ethanesulfonic acid and ethanesulfonic acid hydrate is to be crystallized, low boilers removal is to be carried out such that the starting melt comprising water and ethanesulfonic acid has a concentration of ethanesulfonic acid of 31 to 75 mol %, preferably 45 to 63 mol % and particularly preferably 47 to 55 mol %.

The distillation may be performed in any desired distillation device known to those skilled in the art. The distillation is typically carried out in a distillation column which may comprise internals. Typical internals include, for example, trays or structured or unstructured packings. Useful trays include all known trays, for example sieve trays, bubble trays, tunnel trays or valve trays. Structured packings may be, for example, those made of ceramics materials or plastics materials such as PTFE or PFA. Unstructured packings are, for example, random packings, wherein all commonly used packing elements may be employed, for example those made of ceramics materials, plastic materials such as PTFE or PFA.

The crude alkanesulfonic acid from the production is generally introduced near the top of the distillation column. The low boilers are removed overhead and sent for workup or disposal. A material stream comprising alkanesulfonic acid, high boilers and residual low boilers, in particular water in processes not being water-free or sulfur trioxide in processes being water-free, is withdrawn at the bottom of the distillation column and sent to the melt crystallization as the starting melt. This starting melt is generally a monophasic liquid. This means that the alkanesulfonic acid too is completely comprised in the liquid phase.

Alternatively, however, any other evaporation apparatus known to one skilled in the art may also be used for carrying out the distillation.

Since the distillation and melt crystallization are carried out at different temperatures it is necessary, irrespective of the distillation device employed, to cool the material stream comprising alkanesulfonic acid, high boilers and residual low boilers before it is sent to the melt crystallization. Even when the low boilers removal is carried out at, for example, a subatmospheric pressure of 100 mbar (abs) it is necessary to carry out the distillation with heating in order to establish a bottoms temperature in the range from 160° C. to 191° C. in the case of crystallization of pure methanesulfonic acid and in the range from 86° C. to 112° C. in the case of crystallization of methanesulfonic acid hydrate. Since the melting point of a methanesulfonic acid/water mixture is in the range from −54° C. to +20° C. depending on the water content, appropriate cooling of the bottoms discharge preferably to a temperature just above the melting point of the starting melt must first be effected. Alternatively, it is also possible to supercool the melt before entry into the crystallizer. However such a mode of operation is not preferred since it is difficult to rule out unwanted crystallization in a heat exchanger. When a different alkanesulfonic acid is to be purified the temperatures must accordingly be matched to the boiling point/melting point of the alkanesulfonic acid.

The distillation in step (a) preferably frees the crude alkanesulfonic acid of low boilers to an extent such that, ignoring water in processes not being water-free or ignoring sulfur trioxide in processes being water-free, the proportion of impurities in the material stream comprising alkanesulfonic acid, high boilers and residual low boilers sent to the melt crystallization as the starting melt is not more than 6 wt %, preferably not more than 3 wt %, in the starting melt. It is particularly preferable when the proportion of impurities ignoring water or sulfur trioxide is less than 2 wt %. These indications are merely typical values which moreover depend on the alkanesulfonic acid production process and the high boilers content.

In contrast to the distillation which is carried out at a pressure below atmospheric pressure, the melt crystallization is generally effected at atmospheric pressure. In the case of pure methanesulfonic acid the melt crystallization is preferably carried out at a temperature in the range from −10° C. to 19° C.

The water to methanesulfonic acid ratio in particular is crucial in determining whether the melt crystallization affords pure methanesulfonic acid or the monohydrate of methanesulfonic acid. In what follows, the term impurities refers to the sum of all substances excluding water and methanesulfonic acid.

In order for the melt crystallization to afford pure methanesulfonic acid, i.e. methanesulfonic acid having a proportion of impurities and water of less than 1 wt %, preferably less than 0.5 wt % and in particular less than 0.2%, the melt crystallization is supplied with a material stream comprising alkanesulfonic acid, high boilers and residual low boilers which comprises at least 76 mol %, preferably at least 82 mol % and particularly preferably at least 90 mol % of methanesulfonic acid based on the total amount of methanesulfonic acid and water in the material stream comprising alkanesulfonic acid, high boilers and residual low boilers.

Before recycle streams are fed in, the material stream comprising alkanesulfonic acid, high boilers and residual low boilers moreover comprises not more than 6 wt %, preferably not more than 3 wt % and in particular not more than 2 wt % of impurities based on the total mass of the material stream comprising alkanesulfonic acid, high boilers and residual low boilers. When the substance mixture comprises impurities as well as water and alkanesulfonic acid, the molar concentration ratios of water to alkanesulfonic acid suitable for crystallization do not change substantially. Recycling in the high boilers cycle may cause the concentrations of impurities, for example of sulfuric acid, to exceed the reported values thus reducing the proportion of water. When higher concentrations of impurities are present lower crystallization temperatures are possible and necessary.

To obtain pure methanesulfonic acid the melt crystallization is carried out at a temperature in the range from −50° C. to 19° C. and preferably in the range from −10° C. bis 19° C., more preferably at a temperature in the range from −2° C. to 18° C. and in particular at a temperature in the range from 6° C. to 16° C. High crystallization temperatures are preferred since the energy requirements for the crystallization are thus lower than for lower crystallization temperatures.

To obtain the monohydrate of methanesulfonic acid in a melt crystallization, the material stream comprising alkanesulfonic acid, high boilers and residual low boilers sent to the melt crystallization as the starting melt comprises by preference 31 to 75 mol %, preferably 45 to 63 mol %, particularly preferably 47 to 55 mol % and in particular 48 to 52 mol % of methanesulfonic acid in each case based on the total amount of water and methanesulfonic acid in the material stream comprising alkanesulfonic acid, high boilers and residual low boilers. Here too the proportion of impurities is preferably not more than 6 wt %, more preferably not more than 3 wt % and in particular not more than 2 wt % based on the total mass of the material stream comprising alkanesulfonic acid, high boilers and residual low boilers. When the substance mixture comprises impurities as well as water and alkanesulfonic acid, the molar concentration ratios of water to alkanesulfonic acid suitable for crystallization do not change substantially. These indications are merely typical values which moreover depend on the methanesulfonic acid production process and the high boilers content. When high concentrations of impurities are present lower crystallization temperatures are possible and necessary.

The temperature at which the melt crystallization of the monohydrate of methanesulfonic acid is carried out is in the range from −50° C. to 12° C., preferably in the range from −15° C. to 12° C., more preferably in the range from −8° C. bis 12° C. and in particular in the range from 0° C. bis 12° C. High crystallization temperatures are preferred since they entail lower energy requirements for the crystallization.

For processes being water-free, the sulfur trioxide to methanesulfonic acid ratio is crucial for obtaining pure methanesulfonic acid. In what follows, the term impurities refers to the sum of all substances excluding sulfur trioxide and methanesulfonic acid.

In order for the melt crystallization to afford pure methanesulfonic acid, i.e. methanesulfonic acid having a proportion of impurities and sulfur trioxide of less than 1 wt %, preferably less than 0.5 wt % and in particular less than 0.2 wt %, the melt crystallization is supplied with a material stream comprising alkanesulfonic acid, high boilers and residual low boilers which comprises at least 87 mol %, preferably at least 92 mol % and particularly preferably 93 to 98 mol % of methanesulfonic acid based on the total amount of methanesulfonic acid and sulfur trioxide in the material stream comprising alkanesulfonic acid, high boilers and residual low boilers.

Before recycle streams are fed in, the material stream comprising alkanesulfonic acid, high boilers and residual low boilers moreover comprises not more than 6 wt %, preferably not more than 3 wt % and in particular not more than 2 wt % of impurities based on the total mass of the material stream comprising alkanesulfonic acid, high boilers and residual low boilers. When the substance mixture comprises impurities as well as sulfur trioxide and alkanesulfonic acid, the molar concentration ratios of sulfur trioxide to alkanesulfonic acid suitable for crystallization do not change substantially. Recycling in the high boilers cycle may cause the concentrations of impurities, for example of sulfuric acid, to exceed the reported values thus reducing the proportion of sulfur trioxide. When higher concentrations of impurities are present lower crystallization temperatures are possible and necessary.

To obtain pure methanesulfonic acid the melt crystallization is carried out at a temperature in the range from −50° C. to 19° C. and preferably in the range from −10° C. bis 19° C., more preferably at a temperature in the range from −2° C. to 18° C. and in particular at a temperature in the range from 6° C. to 16° C. High crystallization temperatures are preferred since the energy requirements for the crystallization are thus lower than for lower crystallization temperatures.

The optimal crystallization conditions may vary depending on the type and concentration of the impurities. Said conditions should accordingly be determined by experiment for example. For low concentrations of impurities the crystallization conditions are very close to those for the pure two-substance mixture of water or sulfur trioxide and methanesulfonic acid.

It has been found that both in the production of pure methanesulfonic acid and in the production of the hydrate of methanesulfonic acid a respective proportion of 6 wt % of sulfuric acid based on the total mass of the material stream comprising alkanesulfonic acid, high boilers and residual low boilers is noncritical and has but little effect on the crystallization conditions. It transpires for example that an impurity of 4 wt % of sulfuric acid in a mixture of water and methanesulfonic acid reduces the crystallization temperature of methanesulfonic acid by about 3° C. It further transpires for example that an impurity of 4 wt % of sulfuric acid in a mixture of water and methanesulfonic acid reduces the crystallization temperature of the hydrate of methanesulfonic acid by about 2° C.

The crystallizer in which the melt crystallization is carried out may be any apparatus suitable for performing a crystallization. Heat may be removed from the crystallizer by, for example, jacket cooling or by suitable internals, for example pipes through which a coolant flows, until a temperature low enough for crystallization is achieved. An example of a suitable coolant which in the case of jacket cooling flows through a double wall of the crystallizer or is employed in the throughflowed pipes is a mixture of water and ethylene glycol. It is alternatively possible to carry out direct cooling by means of an evaporating coolant, for example carbon dioxide.

In one embodiment, namely the suspension crystallization method, cooling in the crystallizer converts the starting melt into a suspension comprising alkanesulfonic acid crystals. To achieve this, solid crystals of alkanesulfonic acid may grow directly in the melt thus forming the suspension or alternatively the solid crystals may deposit on a cooled wall from which they are subsequently scraped off and resuspended in the mother liquor. Suitable apparatuses include, for example, stirred tanks, scraped surface coolers or disk crystallizers.

An alternative embodiment comprises carrying out a layer crystallization. Here, the crystallizate is formed as an uninterrupted adherent layer on a cooled surface of the crystallizer. In this case the solid-liquid separation is effected by flow-off of the mother liquor under gravity. The layer crystallization may be carried out either as a static layer crystallization or as a dynamic layer crystallization.

In static layer crystallization the starting melt is charged into a suitable heat exchanger, for example a tube bundle heat exchanger or a plate heat exchanger, and cooled by gradual temperature reduction to partly solidify the starting melt. In a further step the mother liquor is drained and the temperature is increased again. This initially melts off a highly impurified fraction from the crystal layer before the product is melted off in high purity. However the disadvantage of the static crystallization method is the typically low space-time yield since heat and material transport to the deposition surfaces is effected only by free convection. By contrast, dynamic layer crystallization comprises establishing forced convection by pumped circulation of the mother liquor through fully throughflowed pipes, by introduction as a trickle film, by introducing inert gas into a pipe filled with mother liquor or by pulsing.

In suspension crystallization a suspension in which the crystals are suspended in the mother liquor is withdrawn from the crystallizer. Since alkanesulfonic acid is crystallized out of the starting melt the proportion of molten alkanesulfonic acid in the mother liquor withdrawn from the crystallizer is lower than that in the starting melt supplied to the crystallizer. The concentration of impurities in the mother liquor is also higher since these largely do not crystallize. Only the liquid portion, i.e. the liquid phase of the suspension, is referred to as mother liquor.

In order to remove the mother liquor and impurities adhering to the crystals it is possible and preferable to wash the crystals in step (d). This comprises contacting the crystals with a washing liquid with which the impurities are removed.

Any suitable washing means may be used to wash the crystals in step (d). It is possible here to employ a separate washing means or to carry out the solid-liquid separation and washing in one apparatus. One apparatus suitable therefor is, for example, a washing column. In the washing column the crystals to be purified and the washing liquid are preferably run in countercurrent. Since alkanesulfonic acids, in particular methanesulfonic acid, are corrosive it is necessary to configure not only the production apparatuses but also the crystallizer, the apparatus for solid-liquid separation and the washing means in such a way that they are process-durable. It is in particular necessary to avoid the alkanesulfonic acid becoming contaminated by corroded and detached constituents of the apparatus. Suitable corrosion-resistant materials that may be used to fabricate the washing means include, for example, glasses, corrosion resistant steels, enameled steels or plastics materials. Plastics materials may be employed either as facing materials or in a load-bearing capacity. One suitable plastics material is, for example, high density polyethylene or else PTFE. Plastics materials are suitable primarily as a construction material or to provide corrosion insulation of the outer surface of the apparatus. It is possible that some apparatus parts may be under too high a level of mechanical stress for plastics materials. Construction may then be effected in such a way that the stressed plant parts are fabricated from, for example, mechanically stable, enameled steel.

Useful washing liquids include, for example, water, aqueous alkanesulfonic acid, sulfuric acid or other solvents. However, these all have the disadvantage that the crystals of alkanesulfonic acid may be dissolved. Moreover, impurities may also be introduced. It is therefore preferable to employ molten crystallizate as the washing solution instead of the abovementioned washing liquids. The molten crystallizate removes the mother liquor adhering to the crystals and the impurities. Since the molten crystallizate employed as the washing liquid becomes impurified by the mother liquor and by the impurities that are washed off from the crystals and the washing liquid comprises a large proportion of product of value on account of its composition, it is preferable when the molten crystallizate employed as the washing liquid is recycled into the distillation in step (a) or into the melt crystallization after the washing.

When molten crystallizate is used as the washing liquid some of the washing liquid generally also crystallizes on the crystals to be purified.

In order to avoid sedimentation of the crystals from the suspension during transport between the individual apparatuses, in particular between the crystallizer and the washing means, it is preferable to homogenize the suspension. This may be achieved using stirrers or pumps for example. The washing means may either be directly supplied with the suspension withdrawn from the crystallizer while an alternative option comprises subjecting the suspension to processing before it is sent to the washing means. This comprises initially removing the crystals suspended in the mother liquor by mechanical means. This may be achieved using any known separation method for solid-liquid separations. Suitable separation methods include, for example, sieving, pressing, filtration, centrifugation, sedimentation and decantation. After removal of the mother liquor the crystals are resuspended in the washing liquid and the suspension is fed into the washing means.

When molten crystallizate is employed as washing liquid it is preferable when the temperature is selected such that the molten crystallizate for washing the crystals has a temperature 0.1° C. to 15° C. above the solidification temperature of the alkanesulfonic-acid-containing crystallizate. It is preferable when the temperature of the crystallizate employed as washing liquid is 1° C. to 10° C. above the solidification temperature of the alkanesulfonic acid and in particular 2° C. to 4° C. above the solidification temperature of the alkanesulfonic acid.

The washing means is preferably operated such that the residence time of the crystals to be washed in the washing means is in the range from 1 to 25 min. and preferably in the range from 1 to 15 min. However, particularly but not exclusively when the suspension comprising crystals and the molten crystallizate washing liquid are run in countercurrent it has been found that sufficient purification efficacy is achieved even with a residence time of 2 to 8 min.

The crystals may be washed repeatedly to improve purification efficacy. To this end, the washing in step (d) or else the sequence comprising crystallization in step (b), solid-liquid separation in step (c) and washing in step (d) may be performed repeatedly or else operated with partial recycling. However, preference is given to performing crystallization and washing just once. The washing of the crystals may even be eschewed when product purity requirements are low.

The three cited material stream cycles, namely the distillation cycle, crystallization cycle and high boilers cycle pass through plant sectors which in some cases have very different temperature levels. In order to make good use of the energy introduced into the process while furthermore keeping the amount of energy required for heating and cooling the material streams as low as possible it is preferable when the material stream cycles are passed through heat transferrers which transfer heat in countercurrent. For example, the material stream withdrawn from the bottoms discharge of the low boilers distillation and comprising alkanesulfonic acid, high boilers and residual low boilers is cooled before being sent to the melt crystallization while, conversely, the alkanesulfonic-acid-depleted mother liquor recycled into the distillation is heated. It is thus particularly preferable when heat from the material stream comprising alkanesulfonic acid, high boilers and residual low boilers which is to be cooled is transferred to the alkanesulfonic-acid-depleted mother liquor which is to be heated.

When efficient crystallization and washing processes are available, the low boilers and high boilers may be accumulated to high concentrations in the high boilers cycle, i.e. in the recirculating mother liquor, without the crystallized alkanesulfonic acids failing to meet industry purity specifications. It has been found by experiment that total amounts of low boiler and high boiler impurities, excluding water or sulfur trioxide, of up to 6 wt % based on the total mass of the material stream may be tolerated without issue. This allows the stream volumes that are passed through large temperature differences in the high boilers cycle to be kept sufficiently small for the heating and cooling requirements thereof to be small compared to the heat requirements in any case necessitated by the process. The process according to the invention accordingly requires less energy than conventional processes.

Exemplary embodiments of the invention are shown in the figures and are more particularly described in the description which follows.

Figure 1:
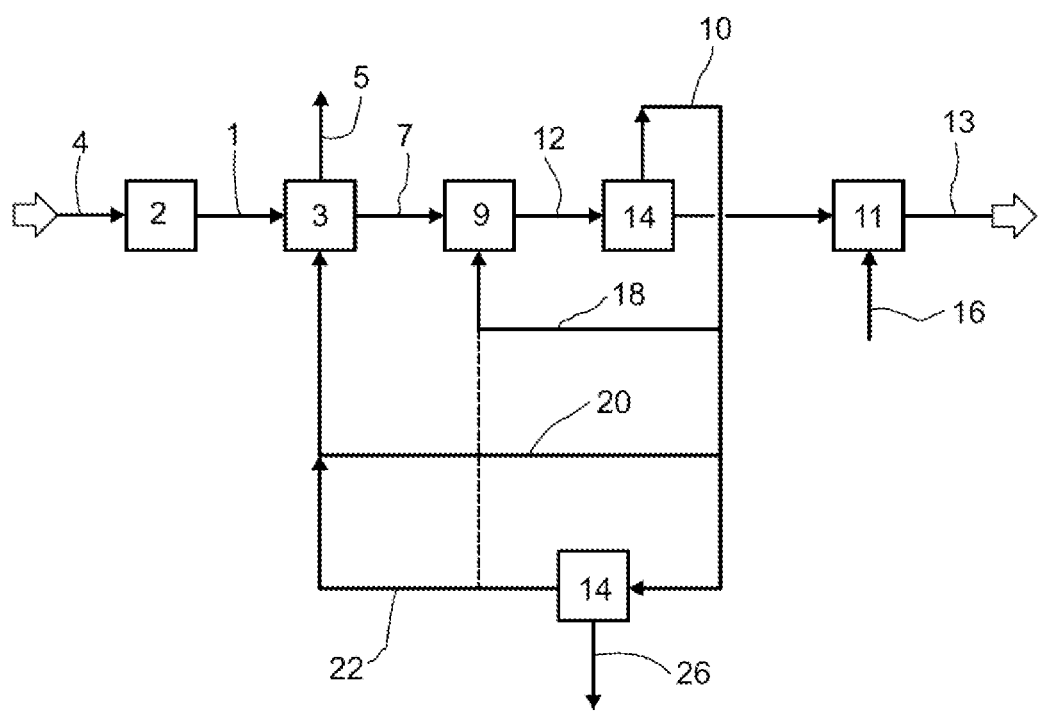
FIG. 1 shows an overview representation of a process for alkanesulfonic acid production.

An overview diagram of a process for alkanesulfonic acid production is depicted in FIG. 1.

A first process step 2 is supplied with starting materials 4 for the production of alkanesulfonic acid. These starting materials 4 depend on the production process. In the first process step 2 crude alkanesulfonic acid 1 is produced. Arranged downstream of the first process step 2 is a low boilers removal 3 in which low boilers are removed from the crude alkanesulfonic acid. A material stream 5 comprising low boilers and a material stream 7 comprising alkanesulfonic acid, high boilers and residual low boilers are withdrawn from the low boilers removal 3. In the low boilers removal 3 an alkanesulfonic acid concentration suitable for crystallization is established in the material stream 7 comprising alkanesulfonic acid, high boilers and residual low boilers.

The material stream 7 comprising alkanesulfonic acid, high boilers and residual low boilers is sent to a melt crystallization 9 as the starting melt. In the melt crystallization 9 the starting melt is part crystallized and a suspension 12 of mother liquor and a crystalline solid phase of alkanesulfonic acid is generated which is sent to a solid-liquid separation 14. In the solid-liquid separation 14 the mother liquor 10 is largely separated from the crystalline solid phase. The solid phase is sent to a washing means 11 in which a washing liquid 16 is used to remove residual mother liquor adhering to the crystals and the product 13 is obtained. The washing liquid is preferably recycled into the melt crystallization or the low boilers removal.

The mother liquor 10 removed in the solid-liquid separation 14 is preferably recycled into the process for purifying alkanesulfonic acids. Possible suitable recycling procedures for the mother liquor 10 are shown by way of example. Thus, for example, in a crystallization cycle 18 mother liquor 10 may be completely or partly recycled into the melt crystallization 9. As an alternative or in addition mother liquor 10 may be completely or partly recycled into the low boilers removal 3 in a distillation cycle 20. It is also possible to remove a high boilers purge stream 26 in a high boilers cycle 22 in a high boilers removal 19 and to recycle the stream thus worked up by removal of the high boilers into the low boilers removal 3 or the melt crystallization 9.

Figure 2:
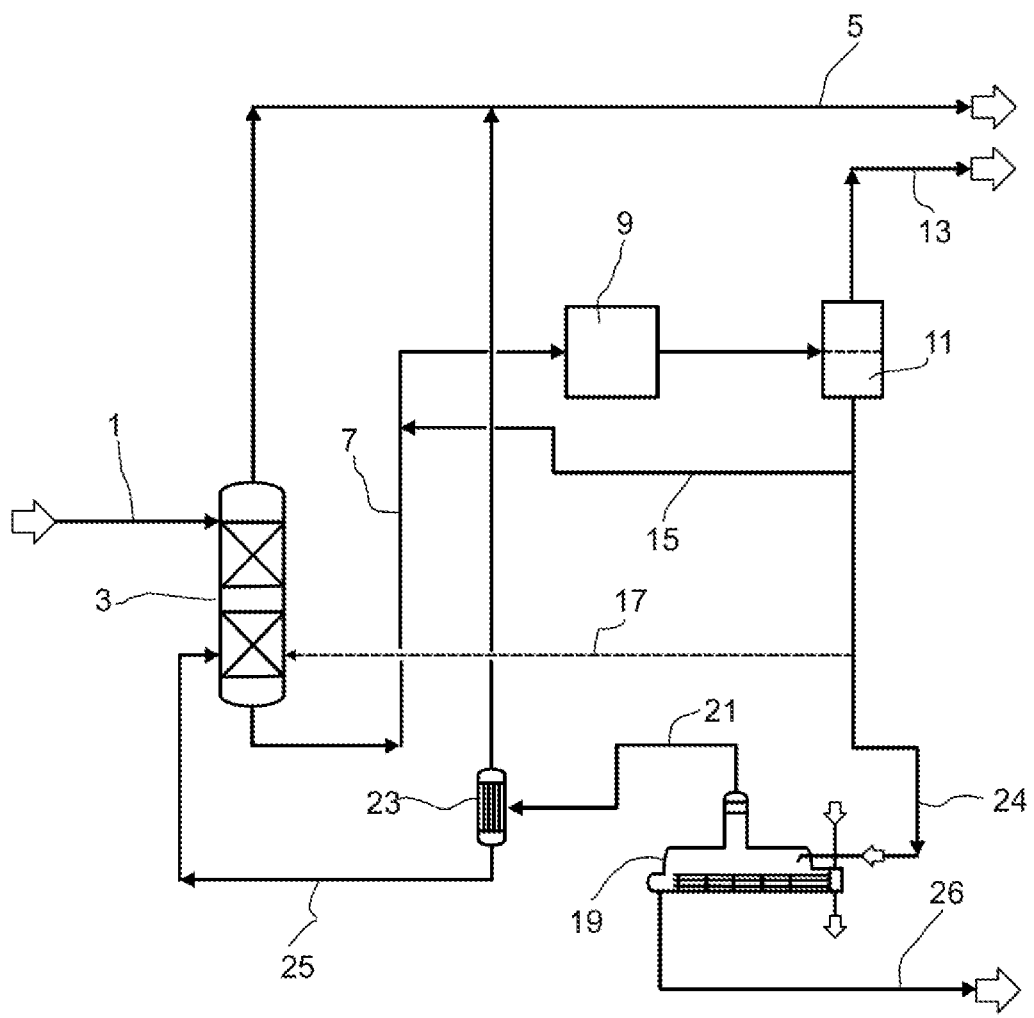
FIG. 2 shows a process flow diagram of the process according to the invention.

FIG. 2 shows a process flow diagram of the process according to the invention.

A melt 1 which comprises crude alkanesulfonic acid and originates from a process for producing alkanesulfonic acid is fed into a low boilers removal 3 for purification. In the low boilers removal 3 low boilers are removed from the crude alkanesulfonic acid. The low boilers removal 3 may be carried out using a distillation column for example. A material stream 5 comprising low boilers is obtained at the top of this distillation column employed for low boilers removal 3. The material stream 5 comprising low boilers is removed from the process and worked up separately or sent for disposal. A material stream 7 comprising alkanesulfonic acid, high boilers and residual low boilers is withdrawn at the bottom of the distillation column employed for low boilers removal 3. Said stream is sent to a melt crystallization 9 as the starting melt. As described hereinabove the melt crystallization 9 may be, for example, a suspension crystallization or a layer crystallization and the melt crystallization may be carried out in any desired crystallizer suitable for the particular crystallization process.

A material stream comprising alkanesulfonic acid crystals and alkanesulfonic-acid-depleted mother liquor is withdrawn from the melt crystallization 9. This material stream is sent to a solid-liquid separation and a washing means 11 in which the alkanesulfonic acid crystals are removed and washed to remove the mother liquor and impurities adhering thereto. To this end it is possible, for example, to run the alkanesulfonic acid crystals suspended in mother liquor in countercurrent to a washing liquid, for example molten crystallizate. The washing liquid washes off the mother liquor and impurities from the crystals. After separation of the crystals from the washing liquid via a solid-liquid separation method a pure product 13 is obtained and withdrawn from the process. If desired, the alkanesulfonic acid obtained may subsequently be diluted to a desired concentration by addition of water.

The washing liquid comprising mother liquor and impurities is likewise withdrawn from the apparatus for solid-liquid separation and washing means 11. Since this material stream still comprises a large proportion of alkanesulfonic acid, said stream is preferably not removed from the process.

It is thus possible, for example, to recycle the washing liquid and alkanesulfonic-acid-depleted material stream withdrawn from the washing means 11 into the melt crystallization 9 as recycle stream 15. This may comprise recycling either the entire stream or merely a substream.

To counter an impermissible level of accumulation of low boilers in this recycle stream, the washing liquid and the alkanesulfonic-acid-depleted stream withdrawn from the washing means may be recycled into the low boilers removal 3 as recycle stream 17. This is advisable particularly when the melt crystallization 9 affords pure alkanesulfonic acid rather than the monohydrate of alkanesulfonic acid as product. By contrast, in the crystallization of the monohydrate a suitable low boilers concentration may alternatively be established by adjusting the bottoms temperature of the distillation column employed for low boilers removal 3. It will be appreciated that another option comprises recycling a substream of the material stream comprising the washing liquid and alkanesulfonic-acid-depleted mother liquor into the melt crystallization 9 as recycle stream 15 and a further substream into the low boilers removal 3.

To remove high boilers from the washing liquid and alkanesulfonic-acid-depleted material stream withdrawn from the washing means, at least some of the mother liquor, the so-called high boilers purge 24, is sent to an evaporator 19 or otherwise utilized. In the evaporator 19 alkanesulfonic acid and low boilers are evaporated and drawn off as vapors 21. The unevaporated portions are withdrawn from the evaporator in liquid form as worked up high boilers purge stream 26 and sent for further use or disposal.

The vapors 21 withdrawn from the evaporator 19 may be recycled into the process for purifying alkanesulfonic acids or may be sent to another application, for example the production of 100 wt % MSA. In the embodiment depicted here the vapors 21 flow into a partial condenser 23. In the partial condenser 23 the alkanesulfonic acid present in the vapors condenses and is recycled into the low boilers removal 3 as condensate 25. Without partial condensation the vapors can only with difficulty be passed directly into the low boilers removal 3 in gaseous form because the evaporator 19 and the distillation column employed for low boilers removal 3 are typically operated at different pressure levels. An alternative recycling option for the condensed vapors is use, after cooling, as washing liquid 16 for the washing means 11.

The uncondensed portion comprising low boilers is withdrawn from the partial condenser 23 in gaseous form and drawn off from the process together with the low-boilers-comprising material stream 5 from the distillation column 3.

When only some of the material stream which comprises washing liquid and depleted mother liquor and is withdrawn from the washing means is fed into the evaporator 19, the remainder may be recycled either into the melt crystallization 9 as recycle stream 15 or into the distillation column 3 as recycle stream 17 or else partly into the melt crystallization as recycle stream 15 and partly into the distillation column 3 as recycle stream 17.

For reasons of energy economy it is advisable to use the smallest possible amount of high boilers purge 24. The lower limit for reducing the amount of high boilers purge 24 is the amount at which just sufficient amounts of high boilers are still discharged from the cycle to keep the concentration of said high boilers below the concentration above which they impede crystallization.

Examples

Crystallization of Methanesulfonic Acid and Methanesulfonic Acid Hydrate

Starting melts 1 to 4 as per table 1 comprising methanesulfonic acid and water as well as defined impurities, for example sulfuric acid, nitric acid, methyl methanesulfonate and chlorine (as total chlorine), were charged at atmospheric pressure and room temperature into a jacketed stirred vessel of 1 l in volume and 150 mm in diameter comprising a close-clearance helical stirrer. The starting melts were then cooled to the respective final temperature specified in table 1 at a cooling rate of 1 K/h.

Crystals were formed during cooling which were kept in suspension by stirring at a rotational speed of 180 min$^{-1}$. Pure methanesulfonic acid was crystallized from starting melt 1 and pure methanesulfonic acid hydrate was crystallized from each of starting melts 2 to 4. The obtained crystals in the suspension were removed on a pressure filter at the respective end temperature and washed with a 70% methanesulfonic acid-water solution to partially remove the mother liquor adhering to the crystals. An amount of washing liquid identical to the amount of crystallizate was chosen.

The proportion of water in the washed crystals and in the mother liquor—apart from in the crystals and in the mother liquor from starting melt 4—was determined by Karl-Fischer titration. The proportions of sulfuric acid and nitric acid in the washed crystals and in the mother liquor were captured by ion chromatography (IC). The proportion of methyl methanesulfonate in the washed crystals and in the mother liquor was determined by gas chromatography (GC). The proportion of total chlorine in the washed crystals and in the mother liquor was determined by Coulometry.

The portions of water and impurities are summarized in tables 2 and 3. Table 4 reports the distribution coefficients of the impurities. The distribution coefficient of a component is the proportion of the component in the crystals divided by the proportion of the component in the mother liquor. Distribution coefficients smaller than 1 show that the proportions of impurity component in the crystals are smaller than the proportion in the mother liquor, i.e. the impurity is depleted by crystallization.

The results reported in table 4 show that, proceeding from the exemplary starting melts 1 to 4, impurities can be removed from methanesulfonic acid and methanesulfonic acid hydrate by crystallization.

It is apparent that depending on purity requirements a further depletion of the impurities in the crystallization is achieved by crystallizing the crystallizate not only once but repeatedly and/or washing it in cocurrent or in countercurrent.

TABLE 1

Compositions and amounts of employed starting melts 1-4 and the respective associated end temperature in the crystallization

| starting melt | 1 | 2 | 3 | 4 |
|---|---|---|---|---|
| total amount [g] | 1250 | 1135 | 1390 | 1080 |
| methanesulfonic acid [wt %] | 96.02 | 81.59 | 79.55 | 83.32 |
| water [wt %] | 1.96 | 15.51 | 15.21 | 15.68 |
| sulfuric acid [wt %] | 1.97 | 1.90 | 4.70 | — |
| nitric acid [wt %] | — | 1 | 0.54 | — |
| methyl methanesulfonate [ppm] | 500 | — | — | — |
| total chlorine [wt %] | — | — | — | not determined |
| end temperature [° C.] | 4 | 6 | 4 | 4 |

TABLE 2

Water and impurities in the mother liquor

| starting melt | 1 | 2 | 3 | 4 |
|---|---|---|---|---|
| water [wt %] | 3.35 | 16.08 | 15.4 | not determined |
| sulfuric acid [wt %] | 3.21 | 3.97 | 8.8 | — |
| nitric acid [wt %] | — | 1.96 | 0.89 | — |
| methyl methanesulfonate [ppm] | 1490 | — | — | — |
| total chlorine [wt %] | — | — | — | 0.5 |

TABLE 3

Water and impurities in the washed crystals

| starting melt | 1 | 2 | 3 | 4 |
|---|---|---|---|---|
| water [wt %] | 1.24 | 17.76 | 17.72 | not determined |
| sulfuric acid [wt %] | 0.48 | 0.47 | 0.85 | — |
| nitric acid [wt %] | — | 0.229 | 0.062 | — |
| methyl methanesulfonate [ppm] | 185 | — | — | — |
| total chlorine [wt %] | — | — | — | 0.034 |

TABLE 4

Distribution coefficients of the impurities

| starting melt | 1 | 2 | 3 | 4 |
|---|---|---|---|---|
| sulfuric acid distribution coefficient | 0.150 | 0.118 | 0.096 | — |
| nitric acid distribution coefficient | — | 0.117 | 0.069 | — |
| methyl methanesulfonate distribution coefficient | 0.124 | — | — | — |
| total chlorine distribution coefficient | — | — | — | 0.068 |

LIST OF REFERENCE NUMERALS 1 crude alkanesulfonic acid
2 first process step
3 low boilers removal
4 starting materials
5 material stream comprising low boilers
7 material stream comprising alkanesulfonic acid, high boilers and residual low boilers
9 melt crystallization
10 mother liquor
11 washing means
12 suspension
13 product
14 solid-liquid separation
15 recycle stream into melt crystallization
16 washing liquid
17 recycle stream into distillation column
18 crystallization cycle
19 evaporator, high boilers removal
20 distillation cycle
21 vapors
22 high boilers cycle
23 partial condenser
24 high boilers purge
25 condensate
26 worked up high boilers purge stream

The invention claimed is:
1. A process for purifying an alkanesulfonic acid, the process comprising:
(a) distilling a melt comprising crude alkanesulfonic acid to completely or partly remove low boilers, wherein the low boilers are drawn off at a top of a distillation column or a one-stage evaporation apparatus and a material stream comprising alkanesulfonic acid, high boilers and residual low boilers is withdrawn at a bottom of the distillation column or the one-stage evaporation apparatus,
(b) sending the material stream into a melt crystallization as a starting melt to form crystals of the alkanesulfonic acid, of hydrates of the alkanesulfonic acid or of a mixture of both the alkanesulfonic acid and the hydrates of the alkanesulfonic acid suspended in mother liquor,
(c) performing a solid-liquid separation to remove the crystals from the mother liquor, and
(d) optionally washing the crystals to remove mother liquor adhering to the crystals.
2. The process according to claim 1, wherein the mother liquor after removal of the crystals and/or the mother liquor generated is/are at least partly recycled into the melt crystallization or into (a).

3. The process according to claim 1,
wherein the mother liquor after removal of the crystals and/or the mother liquor generated is/are at least partly sent into a high boilers removal to remove high boilers from the mother liquor.

4. The process according to claim 3,
wherein the mother liquor after removal of the high boilers is recycled into (a).

5. The process according to claim 3,
wherein the mother liquor after removal of the high boilers is partially condensed and a condensed portion of the mother liquor is recycled into (a) and an uncondensed portion of the mother liquor is discharged from the process as low boilers.

6. The process according to claim 4, wherein the material stream withdrawn from (a) is cooled before being sent to the melt crystallization and the mother liquor which is recycled into (a) is heated.

7. The process according to claim 6,
wherein heat from the material stream is transferred to the mother liquor.

8. The process according to claim 1,
wherein the alkanesulfonic acid is methanesulfonic acid.

9. The process according to claim 1,
wherein the low boilers comprise water or sulfur trioxide.

10. The process according to claim 1,
wherein the material stream sent to the melt crystallization comprises in addition to water or sulfur trioxide not more than 6 wt % of further impurities based on a total mass of the material stream.

11. The process according to claim 1,
wherein the melt crystallization is carried out at a temperature of from −15° C. to 19° C.

12. The process according to claim 1,
wherein the material stream comprises at least 76 mol % of alkanesulfonic acid based on a total amount of alkanesulfonic acid and water in the material stream.

13. The process according to claim 12,
wherein the melt crystallization is carried out at a temperature of from −10° C. to 19° C.

14. The process according to claim 1,
wherein the material stream comprises at least 87 mol % of alkanesulfonic acid based on a total amount of alkanesulfonic acid and sulfur trioxide in the material stream.

15. The process according to claim 14,
wherein the melt crystallization is carried out at a temperature of from −10° C. to 19° C.

16. The process according to claim 1,
wherein the material stream comprises 31 to 75 mol % of alkanesulfonic acid based on a total amount of alkanesulfonic acid and water in the material stream.

17. The process according to claim 16,
wherein the melt crystallization is carried out at a temperature of from −15° C. to 12° C.

18. The process according to claim 1,
wherein the optionally washing comprises washing the crystals with molten crystallizate.

19. The process according to claim 18,
wherein the molten crystallizate for washing the crystals has a temperature of from 0.1° C. to 15° C. above a solidification temperature of an alkanesulfonic-acid-containing crystallizate.

20. The process according to claim 7,
wherein the melt crystallization is a suspension crystallization or a layer crystallization.

* * * * *